(12) United States Patent
Bierer et al.

(10) Patent No.: US 9,193,945 B2
(45) Date of Patent: Nov. 24, 2015

(54) BIOGAS PLANT AND SERVICE DEVICE FOR A BIOGAS PLANT

(75) Inventors: Johann Bierer, Dorfen (DE); Matthias Rabener, Oelde (DE); Andreas Czwaluk, Vechta (DE)

(73) Assignee: UTS Biogastechnik GmbH, Hallbergmoos (DE)

( * ) Notice: Subject to any disclaimer, the term of this patent is extended or adjusted under 35 U.S.C. 154(b) by 315 days.

(21) Appl. No.: 12/977,634

(22) Filed: Dec. 23, 2010

(65) Prior Publication Data

US 2012/0164720 A1 Jun. 28, 2012

(51) Int. Cl.
*C12M 3/00* (2006.01)
*C12M 1/00* (2006.01)
*C12M 1/107* (2006.01)
*B01F 7/00* (2006.01)
*C12M 1/06* (2006.01)

(52) U.S. Cl.
CPC .......... *C12M 21/04* (2013.01); *B01F 7/00733* (2013.01); *C12M 23/26* (2013.01); *C12M 27/02* (2013.01); *Y02E 50/343* (2013.01)

(58) Field of Classification Search
CPC ...... C12M 37/00; C12M 37/04; C12M 33/00; C12M 27/02
See application file for complete search history.

(56) References Cited

U.S. PATENT DOCUMENTS 3,744,593 A * 7/1973 Jones .................. 187/244
5,384,033 A * 1/1995 Matasovic ............ 210/121

FOREIGN PATENT DOCUMENTS

| DE | 197 14 342 C1 | 10/1998 |
| DE | 199 51 959 A1 | 5/2001 |
| DE | 203 05 775 U1 | 7/2003 |
| DE | 10 2006 053 340 A1 | 5/2008 |
| EP | 1 717 305 B1 | 9/2007 |
| EP | 1992405 A1 * | 11/2008 |

OTHER PUBLICATIONS

English translation of EP 1992405.*
English translation of DE 19951959.*
English translation of EP 1717305.*

* cited by examiner

*Primary Examiner* — Nathan Bowers
(74) *Attorney, Agent, or Firm* — Greer, Burns & Crain, Ltd.

(57) ABSTRACT

A biogas plant and a servicing device for a biogas plant having a servicing unit and a servicing section, the biogas plant includes a fermenter tank with a fermentation section and a gas section at an interior space of the fermenter tank. The fermenter tank is closed gas-tight by a gas closing wall disposed at the fermenter tank. The servicing unit is provided with a movable sealing device having at least one retention wall of a flexible material and when installed as intended can be moved between an inoperative position and a sealing position. The sealing device is suitable to separate the servicing section substantially gas-tight from the gas section in the sealing position.

10 Claims, 2 Drawing Sheets

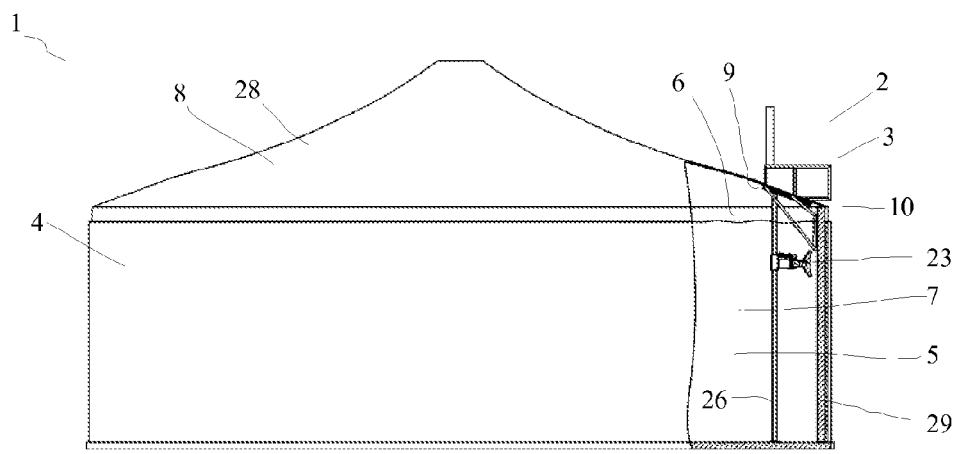
Fig. 1
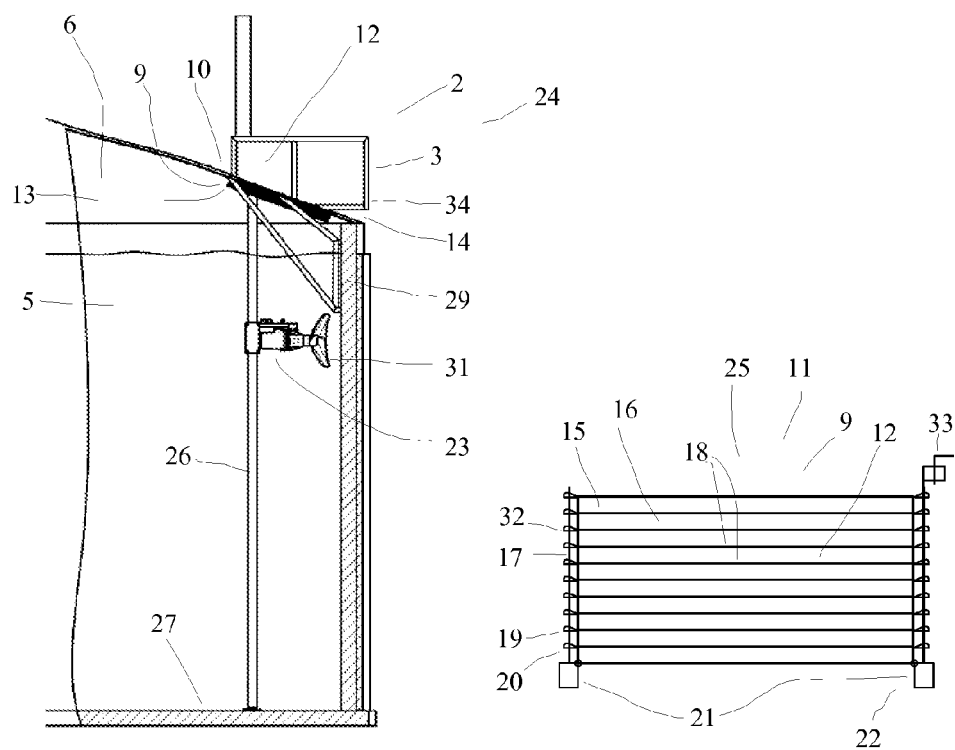
Fig. 2
Fig. 3

BIOGAS PLANT AND SERVICE DEVICE FOR A BIOGAS PLANT

BACKGROUND

The present invention relates to a biogas plant and a servicing device for a biogas plant.

Various biogas plants and servicing devices for biogas plants have become known in the prior art. Biogas plant are as a rule provided with one or more fermenter tanks for fermenting the fermenting substrates and as a rule with an agitator provided for stirring and at least partially homogenising the fermenting substrates in the fermenter tank.

Most of these agitators have agitator blades with which to mix and agitate the fermenting substrates. In dependence on the substrates to be fermented and further ambient conditions and on the materials employed the agitators require inspection and if necessary maintenance at specified intervals. Some or all of the agitator blades may be exchanged for example.

For maintenance on an agitator the agitator which is disposed on a mounting or holding rod or the like is traversed from the lower fermentation section in which the fermenting substrates are located, to the upper gas section. For gaining access to the agitator, for example a biogas plant equipped with a flexible top sheeting may be opened and the top sheeting removed entirely to thus gain easy access to the agitator. This method, however, involves the drawback of considerable work for removing the top sheeting. Also, the biogas collecting in the gas section above the fermentation section escapes as the top sheeting is removed.

For biogas plants having a concrete top, DE 199 51 959 A1 has made known a rectangular maintenance shaft inserted in the concrete top allowing maintenance of the agitator without significantly compromising the gas production. In the case of fermenters having a high solids content the maintenance shaft is bipartite with the top part terminating approximately 10 cm above the normal liquid level. In the case of maintenance a lower shaft portion is inserted into the top shaft portion for immersing in the fermenter mass. For sealing the top shaft portion is provided with a circumferential sealing channel with which when assembled a sealing collar of the lower shaft portion engages. These two-part maintenance shafts involve the drawback that each case of maintenance requires newly inserting the lower shaft portion and sealing against the top shaft portion and removing again after maintenance. Also, the fermenter filling volume must be kept within narrow limits for achieving reliable sealing. Therefore this document proposes for fermenters having a low solids content a one-piece maintenance shaft reaching at least 10 cm beneath the normal liquid filling level. For balancing the gas a shut-off pipe connection to the gas headspace of the fermenter is provided. In the case of maintenance the work involved is reduced compared to a two-piece maintenance shaft. The drawback of this is, however, that these maintenance shafts are suitable for low solids contents only. Also, deposits may accumulate on the immersed shaft. Another drawback is a permanent increase in the agitating resistance and thus in energy consumption.

EP 1 717 305 B1 has made known a biogas plant servicing shaft for a fermenter of a biogas plant with a top sheeting with the servicing shaft being provided as a gas-tight, dome-shaped cover across a servicing opening in the fermenter tank cover. The agitating unit held vertically in the fermenter tank can be moved upwardly from the lower fermentation section into the servicing shaft interior. After opening a servicing flap at the servicing shaft the agitator device can be serviced in the interior of the dome-type servicing shaft and one or all of the agitator blades may be exchanged as needed.

A biogas plant servicing shaft according to EP 1 717 305 B1 operates reliably, allowing servicing the agitator device while involving little work wherein maintenance does not require removal of the entire top sheeting. However, as the servicing flap is opened, the biogas which has collected in the upper gas section of the fermenter tank and which is under overpressure, escapes while air and thus a considerable amount of oxygen enters the fermenter tank requiring removal prior to restarting operation.

SUMMARY

In view of the described prior art it is therefore the object of the present invention to provide a servicing device and a biogas plant having a servicing device involving ease of operation and ease of maintenance while minimizing biogas losses when carrying out maintenance.

The servicing device according to the invention comprises a servicing unit and a servicing section and it is provided to be used in a biogas plant which biogas plant comprises at least one fermenter tank wherein an interior space of the fermenter tank is provided with at least one fermentation section and at least one gas section. The fermenter tank is sealed substantially gas-tight by at least one gas closing wall disposed at the fermenter tank. The servicing unit is provided with at least one movable sealing device which when installed as intended can be moved at least between an inoperative position and a sealing position. The sealing device comprises at least one retention wall of a flexible material. The sealing device is suitable to separate the servicing section from the gas section substantially gas-tight in the sealing position, at least while the biogas plant is in use as intended.

The servicing device according to the invention has many advantages. One considerable advantage of the servicing device according to the invention is that in the sealing position the servicing section is sealed gas-tight from the gas section by the flexible retention wall. The flexible retention wall allows maintenance on an agitator with a variable fermenter mass filling level. Ease of maintenance is provided. The flexible length of the retention wall allows a flexible adjustment to the currently prevailing conditions. Concurrently the sealing device is provided at the servicing device including in the inoperative position and does not require removal every time after maintenance. In the inoperative position the sealing device is typically mostly provided above the liquid level and is at least not substantially immersed in the liquid. This prevents a greatly increased flow resistance. Also, converting and installing components is not required for every maintenance.

The invention allows uncomplicated and easy maintenance on an agitator or an agitator device located in the servicing section while at the same time prohibiting the biogas located in the gas section of the fermenter tank from escaping to the exterior through the servicing section of the servicing unit. This allows uncomplicated maintenance involving minor losses of gas. Moreover no—or only minor quantities of—oxygen can enter from the exterior during maintenance which requires removal at restarting to ensure the proper methane content.

Moreover the scouring period during which fresh air is fed to the servicing section to avoid explosive gas mixtures can be kept very brief. Furthermore, after a performed maintenance the biogas plant can be restarted immediately without removing any components which on the whole causes considerably lower costs and losses.

In a preferred more specific embodiment of the invention the servicing section is connected with the gas section to be gas-permeable at least in the inoperative position of the sealing device. This means that during normal operation of the biogas plant the servicing section is connected with the gas section at least in part and in particular entirely so as to allow the biogas produced by the fermenting substrates to collect in the servicing section as well. For normal operation the flexible retention wall is pulled upwardly so as to not form a separate gas headspace at the servicing unit.

Preferably the sealing device is attached at the servicing unit. In an advantageous configuration the servicing unit is provided with at least one attachment frame with the sealing device fixed to the attachment frame. The attachment frame is in particular provided to be sealingly attached to the gas closing wall or the tank cover of the biogas plant.

In particular is the attachment frame attached to a carrying console of the servicing unit. The servicing unit may for example be configured as or comprise a servicing shaft. A servicing platform may be provided, the servicing platform and the servicing unit in particular being supported by the carrying console. The carrying console may be attached to the tank wall of the fermenter tank. Attachment of the carrying console is conceivable to the inner tank wall or else to the outer tank wall. It is likewise possible to support the carrying console on a separate foundation external of the fermenter tank.

The sealing device is in particular approximately channel-shaped when in the sealing state. Particularly preferably does the retention wall consist at least in part of a gas-tight web, a film hose or the like.

All of the configurations particularly preferably provide for the sealing device to extend longer in the sealing position than in the inoperative position. In the sealing position the sealing device is preferably at least 50% longer and in particular more than twice as long as in the inoperative position. This means that the servicing section which is preferably provided inside the sealing device at least in part, extends considerably longer in the sealing position than in the inoperative position.

It is preferred for the sealing device to comprise bellows.

The sealing device may be telescopically extendable and may for example comprise slightly conical and flexible or gas-tight, flexibly interconnected cylinder segments which are telescoped. This does not require for the sealing body to be shaped cylindrically but its cross-section may be rectangular or polygonal or otherwise. What is significant is that the retention wall is configured substantially gas-tight at the sealing device when the sealing device is in the sealing position.

Preferably at least one displaceable guide member is provided which may for example be configured as a guide rope or a guide chain. The sealing device is preferably displaceable by means of the guide member where the retention wall of the sealing device can be lowered by the guide member at least from the inoperative position to the sealing position.

A flexible guide member and a flexible retention wall offer considerable advantages since retracting the guide member causes the guide wall to contract such that it requires little space in the inoperative position.

Preferably the sealing device is provided with at least one mounting frame or mounting unit to spread the retention wall. Such a mounting unit or such a mounting frame allows to maintain the cross-section of the sealing device substantially unchanged whether the servicing device with the sealing device is in the inoperative position or in the sealing position.

At this point reference is made to the fact that the term "inoperative position" of the sealing device is understood to mean a position in which the sealing device is inactive while the biogas plant itself may certainly be in operation which it usually is. The sealing device is, however, displaced into the sealing position when maintenance is intended to be performed on the servicing device or for example on an agitator in the servicing section of the servicing device.

Preferably a number of mounting units or mounting frames are provided which spread the retention wall of the sealing device at predefined intervals or in spaced-apart positions. The particular mounting units or mounting frames may be interconnected although they may be separately provided at the retention wall. It is as well conceivable for a mounting unit to comprise a coiled mounting wire or the like with which to spread the sealing device wherein the mounting unit retains the cross-section approximately constant while the retention wall is longitudinally displaceable. The cross-section is in particular dimensioned for the agitator device to pass through.

In advantageous more specific embodiments at least one weighting device is connected with the lower end of the sealing device. This allows that as the guide member is relieved the sealing device is transferred from the inoperative position to the sealing position.

For example when the flexible guide member is configured as a rope or the like and is at least partially wound up in the inoperative position, then unwinding the guide member may cause the lower end of the sealing device to automatically move downwardly when a weight is provided at the lower end of the sealing device. In this way the sealing device is automatically transferred from the inoperative position to the sealing position as the flexible guide member is allowed to descend. Transferring the sealing device from the sealing position to the inoperative position can be done by retracting or winding up the flexible guide member.

A crank mechanism is preferably connected with the guide member for descending or retracting the flexible guide member.

Preferably the sealing device is disposed at the servicing device in the inoperative position.

Preferably the flexible guide member is guided at the sealing device in eyelets or the like. As the flexible guide member is retracted, it contracts the retention wall of the sealing device.

The biogas plant according to the invention is equipped with at least one fermenter tank and comprises a fermentation section provided in an interior space of the fermenter tank and a gas section. The fermenter tank is sealed substantially gas-tight by a gas closing wall or a tank cover. At least one agitator device and at least one servicing device with a servicing section are provided which agitator device can be transferred at least from an operating position in the fermentation section to a maintenance position in the servicing section of the servicing device. At least one movable sealing device with at least one retention wall of a flexible material is provided which is displaceable between an inoperative position and a sealing position wherein when in the sealing position the sealing device separates the servicing section from the gas section substantially gas-tight.

The biogas plant according to the invention also has many advantages. By way of the servicing device with the movable sealing device a biogas plant is provided in which the sealing device is readily displaceable between an inoperative position and a sealing position. Maintenance can be carried out without requiring extensive installing and removing of components. Transfer between the inoperative position and the sealing position can be done independently of the filling level in the fermenter. This allows a gas-tight separation of the servicing section of the servicing device from the gas section of the biogas plant so as to dispense with releasing the entirety of the biogas accumulated in the gas section of the fermenter tank for carrying out maintenance or repairs for example on an agitator present in the servicing section.

The biogas plant is in particular equipped with a servicing device as it has been described above.

In a simple configuration the biogas plant virtually consists of the fermenter tank and the tank cover provided thereat, and of the servicing device and an agitator device. The biogas produced by the fermenting substrates is collected and may be discharged if required through a dedicated gas pipe.

Particularly preferably the agitator device is held vertically adjustable at a mounting rod or holding rod or the like. This enables transfer of the agitator device from the operating position to a maintenance position. The operating position will typically be located within the fermentation section of the fermenter tank and the maintenance position, above the fermentation section. The maintenance position may be provided within the gas section or even above the tank cover. The maintenance position is for example provided above the tank cover when a servicing shaft or the like extending above the tank cover is provided, wherein for maintenance the agitator device is transferred from the lower fermentation section to the upper servicing section to carry out maintenance.

Then the holding rod will as a rule extend within the servicing section from the fermentation section into the gas section and optionally from there into the interior of the servicing shaft and even beyond.

In a particularly simple configuration the servicing device is equipped with a servicing opening which servicing opening may be located on the surface of the tank cover or the gas closing wall or it may be provided therein. This structure does not necessarily require a dome-shaped servicing shaft configuration. Then the section in which maintenance is carried out may be provided above the gas closing wall or the tank cover in the open air. To this end the agitator device is transferred on the mounting rod or holding rod from the fermentation section upwardly as far as above the tank cover while the sealing device reliably seals the servicing section inside the tank from the gas section.

The gas closing wall may be formed by the single- or double-walled tank cover. It is also conceivable for the gas closing wall to be provided as a gas holder sheeting beneath the actual tank cover. It is conceivable to configure the tank cover as a top sheeting which may be provided for or prohibited from being walked on. It is also conceivable for the tank cover to be configured at least in part as a rigid cover, e.g. as a concrete roof or concrete ceiling. In the case of a concrete roof or concrete ceiling the gas closing wall is as a rule formed by the concrete roof or concrete ceiling itself.

In all of the configurations the servicing device preferably comprises a carrying console for supporting the servicing device in particular on the inner or outer tank wall. A servicing shaft, if provided, is preferably also supported by the carrying console.

Preferably the sealing device is disposed and retained at the servicing device in the inoperative position. In the sealing position the sealing device preferably extends from the servicing device downwardly at least as far as the fermentation section. The sealing device may as well extend as far as beneath the fermentation section surface. It is also conceivable for the sealing device to lie on the fermentation section, its edges being slightly immersed in the fermentation section to allow the tightest possible connection of the sealing device with the fermentation section. The edge may for example be immersed in the fermenter mass approximately 2 cm to 5 cm.

In all of the configurations it is preferred for the sealing device to surround at least part of the holding rod or the mounting rod at least in the sealing position. This ensures that in the case of height displacement the agitator device moves up and down inside the sealing device and does not need to penetrate the retention wall such that an additional sealing at the mounting or holding rod can be omitted.

As was described above, a mounting unit or a mounting frame or a number of these mounting units or mounting frames may be provided for spreading the sealing device in the sealing position.

On the whole the sealing device forms a gas curtain separating the biogas section in the fermentation tank from the servicing section. Although the actual maintenance of the agitator or an agitator device may be done inside the tank, it may as well be carried out on the roof or above the roof of the fermenter tank cover.

In all of the cases normal operation of the biogas plant provides for the sealing device to be pulled up with the retention wall. For performing maintenance on the agitator the agitator may be pivoted towards the outer wall and rotated upwardly by way of the height displacement for example as far as the stopper. Subsequently or concurrently the sealing device retention wall which serves as a gas curtain may be lowered by means of the guide members of the provided or additional weights at the retention wall until it reaches and is perhaps slightly or even deeper immersed in the fermenting substrate.

Subsequently the maintenance cover or the servicing opening of the servicing device may be opened and the gas still remaining in the servicing section, allowed to escape. Then the agitator can be rotated upwardly until it is for example located above the tank cover where maintenance is performed. At the same time the biogas present in the gas section of the fermenter tank is retained by the retention wall serving as a gas film so as to cause virtually no loss of gas while concurrently allowing more comfortable maintenance work. After maintenance the agitator device can be lowered, the servicing opening closed, and the sealing film or gas sheeting, pulled back up and secured. Subsequently the plant can continue normal operation.

To reinforce the retention wall of the sealing device a tube or a carrier or mounting unit may be provided at the lower edge or in specific intervals to reinforce and spread the retention wall. For automatically or manually pulling up the retention wall, closable tubes or the like are mounted to the corners of the servicing opening of the servicing device through which the flexible guide member may be threaded.

BRIEF DESCRIPTION OF THE DRAWINGS

Other advantages and features of the present invention can be taken from the exemplary embodiment which will be described below with reference to the accompanying figures:

These show in:

FIG. 1 a schematic side view of a biogas plant according to the invention with a sectional detail view of a fermenter tank;

FIG. 2 an enlarged illustration of the servicing device of the biogas plant in FIG. 1;

FIG. 3 a schematic illustration of the sealing device of the servicing device in FIG. 2;

DETAILED DESCRIPTION

Figure 4:
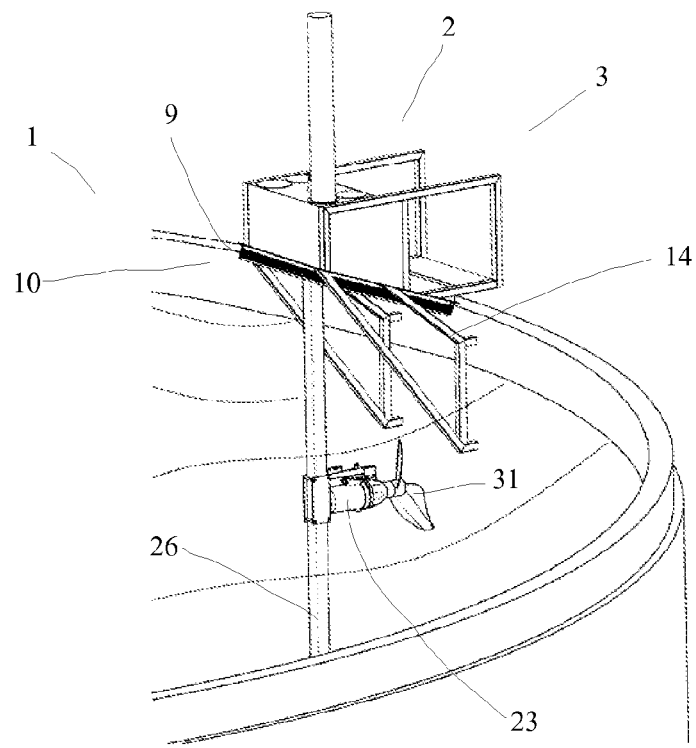
FIG. 4 a schematic, enlarged view of the servicing device in the inoperative position.

With reference to the FIGS. 1 to 5 an embodiment of the biogas plant 1 with a servicing device 2 will be explained below.

The biogas plant 1 illustrated in a side view in FIG. 1 comprises a fermenter tank 4 in which a fermentable substrate for manufacturing biogas is located in the lower fermentation section 5 wherein the biogas manufactured collects in the gas section 6 above the fermentation section 5.

The fermenter tank 4 comprises a tank wall 29 and a tank cover 8 which in the present case is configured as a flexible top sheeting 28. The present top sheeting 28 forms the gas closing wall 8.

For agitating the fermenting substrate in the interior space 7 of the fermenter tank 4 in the fermentation section 5 and for promoting the fermentation process, at least one agitator is provided as an agitator device 23 which is or are disposed at a holding rod 26 extending from the bottom 27 of the fermenter tank 4 as far as above the tank cover 28.

The fermenter tank 4 is provided with at least one servicing device 2 configured as a servicing unit or a servicing shaft 3.

The servicing shaft 3 illustrated in the present embodiment is supported on a carrying console 14 on the inside of the tank wall 29.

The servicing shaft 3 comprises a platform 34 for a person to stay on to perform maintenance. The servicing unit 2 is connected with the top sheeting 28 or the gas closing wall 8 so as to be gas-tight.

In the position illustrated in FIGS. 1 and 2 the sealing device 9 is in the inoperative position 10 in which the retention wall 15 of the sealing device 9 is disposed contracted at the attachment frame 13 of the servicing device 2. In the inoperative position 10 the sealing device 9 requires little space. This position is provided for normal operation of the biogas plant 1 wherein the agitator device 23 agitates the fermenting substrate in the fermentation section 5 while the biogas produced collects above the fermentation section 5 in the gas section 6.

The present sealing device 9 comprises a retention wall 15 which on the whole is configured as bellows 16 and which can be transferred from the position illustrated in FIG. 2 to the telescoped position illustrated in FIG. 3. FIG. 3 illustrates the sealing device 9 in the sealing position 11. Presently this is achieved in that the flexible guide members 17 configured as ropes are lowered via the crank mechanism 33 wherein the dead weight of the sealing device 9 or else additional weights 21 cause the retention wall 15 to descend. The retention wall 15 may be spread via additional mounting units 18 located on the retention wall at specified intervals. The retention wall 15 is connected with the guide member 17 configured as a rope via attachment eyelets 32.

When the guide member 17 is descended then the dead weight or the additional weights 21 cause the retention wall 15 to lower until the retention wall 15 reaches the surface of the fermentation section 5 and may be immersed somewhat. This achieves a tight closing of the servicing section 12 located inside the sealing device against the gas section 6.

In this sealing position 11 maintenance can be performed. To this end the agitator device 23 is traversed outwardly towards the tank wall where it is pivoted and then raised until it is located above the fermentation section in the servicing section 12 which by way of the lowered retention wall 15 is separated from the gas section 6 so as to be gas-tight.

In the illustrated embodiment the agitator device 23 is transferred as far as above the tank cover 28 until it is located within that portion of the servicing section 12 provided inside of the servicing shaft 3. There the servicing opening may be opened subsequently and after allowing any biogas still present in the servicing section to escape the agitator device is comfortably accessible for maintenance.

The sealing device may be articulated on one side while the other side is pivotal for transferring the retention wall between the inoperative position 10 and the sealing position 11. It is possible for the pivot point to be slightly disposed at the level of the maximum filling level or slightly below wherein the larger part and in particular at least half, three quarters or more of the sealing device 9 is located above the fermenter mass in the inoperative position 10.

In an alternative configuration the servicing shaft for example does not extend dome-like above the tank cover but in a simple case a servicing opening is provided in the tank cover which after opening allows raising the agitator device as far as above the tank cover whereupon maintenance can be done on the agitator device the open air above the tank cover 28.

FIG. 4 again shows the operating position where the sealing device is in the inoperative position 10 and the biogas plant may be in normal operation. To allow a better view the top sheeting is illustrated transparent to offer a view into the interior of the fermenter tank 4.

Figure 5:
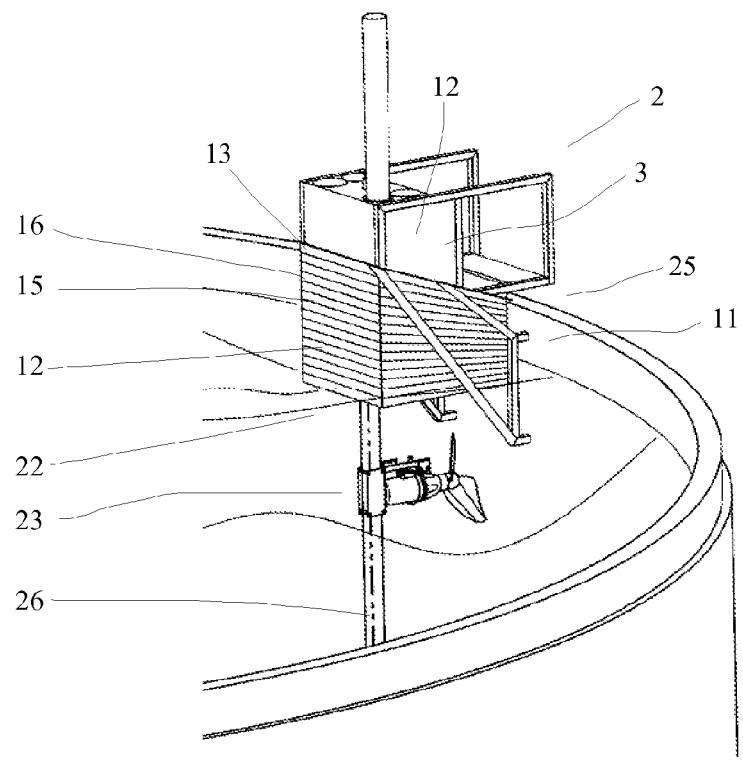
FIG. 5 an illustration of the servicing device in the sealing position.

FIG. 5 similarly illustrates the sealing position 11 in which maintenance 25 may be performed. The retention wall 15 of the sealing device 9 which serves as a gas curtain has been lowered as far as the level of the fermentation section 5.

On the whole the invention allows particular ease of maintenance on an agitator device and other components. Performing maintenance involves very minor loss of gas while also a minimum of oxygen enters the plant. Employing the invention is also efficient in terms of economics.

LIST OF REFERENCE NUMERALS 1 biogas plant
2 servicing device
3 servicing unit, servicing shaft
4 fermenter tank
5 fermentation section
6 gas section
7 interior space
8 gas closing wall, tank cover
9 sealing device
10 inoperative position
11 sealing position
12 servicing section
13 attachment frame
14 carrying console
15 retention wall
16 bellows
17 guide member
18 mounting frame
19 position
20 position
21 weighting device
22 end
23 agitator device
24 operating position
25 maintenance position
26 holding rod
27 bottom
28 top sheeting
29 tank wall
30 displacement device
31 agitator blade 32 attachment eyelet
33 crank mechanism
34 platform

The invention claimed is:

1. A servicing device comprising: a stationary servicing unit and a stationary servicing section provided to be employed in a biogas plant, the biogas plant having at least one fermenter tank including a fermentation section with a fermenting substrate, and a gas section at an interior space of the fermenter tank which the fermenter tank is closed substantially gas-tight by at least one gas closing wall disposed at the fermenter tank, at least one sealing device is provided which is suitable to effect a substantially gas-tight separation of the servicing section from the gas section, the sealing device includes at least one retention wall of a flexible material having an end, and when installed as intended, said end of said at least one retention wall is movable at least between an inoperative position outside of the fermenter tank, and a sealing position inside the fermenter tank, wherein the retention wall is fully contracted in the inoperative position and not in contact with the fermentation section, and moves to a telescoped position in the sealing position in which the retention wall reaches the surface of the fermentation section and is at least partially immersed in the fermenting substrate.

2. The servicing device according to claim 1 wherein the servicing section is connected with the gas section to be gas-permeable in the inoperative position.

3. The servicing device according to claim 1 wherein the servicing unit comprises an attachment frame and the sealing device is attached to the attachment frame.

4. The servicing device according to claim 3 wherein the attachment frame is attached to a carrying console of the servicing unit.

5. The servicing device according to claim 1 wherein the sealing device comprises bellows and wherein the sealing device is in particular longer in the sealing position than in the inoperative position.

6. The servicing device according to claim 1 further comprising at least one displaceable guide member wherein the sealing device is displaceable, and wherein the retention wall of the sealing device can be descended by the guide member at least from the inoperative position to the sealing position.

7. The servicing device according to claim 1 wherein at least one mounting frame is provided at the sealing device for spreading the retention wall wherein multiple mounting frames are provided at the sealing device which spread the retention wall in multiple positions spaced apart from one another.

8. The servicing device according to claim 1 wherein at least one weighting device is connected with the lower end of the sealing device to transfer the sealing device from the inoperative position to the sealing position as the guide member is relieved.

9. The servicing device according to claim 1 wherein the sealing device is disposed at the servicing device in the inoperative position.

10. A servicing device comprising: a servicing unit and a servicing section provided to be employed in a biogas plant, the biogas plant having at least one fermenter tank including an agitator device in a fermentation section with a fermenting substrate, and a gas section at an interior space of the fermenter tank which the fermenter tank is closed substantially gas-tight by at least one gas closing wall disposed at the fermenter tank, at least one sealing device is provided which is suitable to effect a substantially gas-tight separation of the servicing section from the gas section, the sealing device includes at least one retention wall having an end, said at least one retention wall being made of a flexible material and being independent of and thereby independently movable relative to the agitator device, and when installed as intended, said end of said at least one retention wall is movable at least between an inoperative position outside of the fermenter tank, and a sealing position inside the fermenter tank, wherein the retention wall is fully contracted in the inoperative position and not in contact with the fermentation section, and moves to a telescoped position in the sealing position in which the retention wall reaches the surface of the fermentation section and is at least partially immersed in the fermenting substrate.

* * * * *